United States Patent [19]

Bartoli et al.

[11] 4,336,357

[45] Jun. 22, 1982

[54] SUPERFICIALLY HYDROLYZED BIOCOMPATIBLE POLYAMIDE MATERIAL

[75] Inventors: Francesco Bartoli, Rome; Walter Marconi, San Donato Milanese; Franco Morisi; Francesco Pittalis, both of Rome, all of Italy

[73] Assignee: Snamprogetti, S.p.A., Milan, Italy

[21] Appl. No.: 172,957

[22] Filed: Jul. 28, 1980

Related U.S. Application Data

[63] Continuation of Ser. No. 26,892, Apr. 4, 1979, abandoned.

[30] Foreign Application Priority Data

Apr. 12, 1978 [IT] Italy .............................. 22222 A/78

[51] Int. Cl.$^3$ ............................................. C08G 69/48
[52] U.S. Cl. .............................. 525/420; 128/DIG. 3; 210/321.1; 525/419; 528/310; 528/323; 528/335
[58] Field of Search ................................ 525/420, 419

[56] References Cited

U.S. PATENT DOCUMENTS 2,876,524  3/1959  Reyerson et al. .................... 525/420
3,011,915 12/1961  Sklar .................................... 525/420
3,060,550 10/1962  Smith .................................... 525/420
3,075,823  1/1963  Reyerson et al. .................... 525/420
3,843,617 10/1974  Orlov et al. .......................... 525/420

OTHER PUBLICATIONS

Bruck et al., Biomat., Med. Dev. Art. Org. 1 (II), (1973), pp. 191–222.
Bruck, J. Biomed. Mat. Res. Symposium No. 8, (1977), pp. 1–21.
Simon, Trans. Amer. Soc. Art. Int. Organs, XXI, (1975), pp. 49–54.
Scand. J. Haemat, (1970), pp. 374–382.
Nature, vol. 249, pp. 81–83, (May 1974).

*Primary Examiner*—Harold D. Anderson
*Attorney, Agent, or Firm*—Morgan, Finnegan, Pine, Foley & Lee

[57] ABSTRACT

Polyamide materials for the construction of protheses and surgical sundries are made biocompatible by inducing a superficial hydrolysis by treating such materials, either raw or in the form of shaped articles, with a normal multiple solution of hydrogen chloride. Thrice normal or fourfold normal solutions are preferred and the treatment time being a function of the temperature. At human body temperature (37° C.) a treatment time from 30 to 60 minutes will do.

9 Claims, No Drawings

SUPERFICIALLY HYDROLYZED BIOCOMPATIBLE POLYAMIDE MATERIAL

This is a continuation, of application Ser. No. 026,892, now abandoned filed Apr. 4, 1979.

This invention relates to a process for the preparation of biocompatible materials of a polyamide type; it relates, in addition, to the products thus obtained.

The use of polymeric materials in the biomedical art has become more and more widespread in the last years.

One of the major hindrances against an ever wider use of such materials is their usually poor compatibility with blood. For this reason, materials which have now attained appreciable mechanical properties and which would be extremely useful in artificial protheses, do not find, in the actual practice, an application on account of their high tendency towards the formation of thrombi. Nylon is an example, which, on account of its mechanical properties, would find a wide application in the field referred to above, should it not be extremely prone to the formation of thrombi.

The problem of the thrombogenic nature of the polymeric materials has invited many searchers to try and find out the origins. More particularly, the properties of the surfaces have been studied in order to find out a possible correlation between them and the materials in question when placed in contact with blood.

A few authors have tried to correlate the thrombogenic nature of the polymeric materials with the surface tension or the Z potential. See, for example, the articles by S. D. Bruck in Biomat., Med. Dev. Art. Org. 1, 191, 1973 and in J. Biomed. Mat. Res. Symposium No. 8 page 1 (1977), from which it would appear that the biocompability of a few materials such as polyurethans may be correlated with a negative Z-potential measured in vitro using the Krebs solution, and with a critical surface tension below 30 dynes/cm.

It is generally believed that a material having a negative surface charge has good chances of being biocompatible, on account of the fact the blood platelets have a negative surface charge.

Another parameter which is generally accepted in evaluating the materials is the capacity of selectively adsorbing a few proteins on the surface when placed in contact with blood.

In this connection, see the article by D. J. Simon, in Trans. Amer. Soc. Art. Int. Organs, XXI, 49, 1975 wherein the lack of adhesion of the platelets to several materials such as polyurethans, silastic resins and Teflon (Reg. Trade Mark) is correlated with the preferential adsorption of albumin as compared with globulins and fibrinogen.

It is likewise known that polyamide substrates can be hydrolized in order to set free completely the amine and carboxyl groups, but it has proven extremely difficult to carry out such a hydrolysis in such a way as to obtain a final product which is only partially modified.

It is thus extremely surprising that the present applicants have succeeded in carrying out a unique superficial hydrolysis of the starting materials and concurrently obtaining biocompatible materials which can be employed for the purposes indicated above without suffering of any of the shortcomings aforementioned.

As a matter of fact, the object of the present invention is to provide a process for the superficial hydrolysis of polyamide materials, which permits to obtain materials which are only partially modified and exhibit a high degree of biocompability.

Such a reaction is carried out by carefully checking the hydrolizing agent and the reaction conditions. More particularly, hydrochloric acid is used as a concentration of from 3 to 4-normal and the temperature is maintained in the interval from 20° C. to 40° C. Substantially all unreacted hydrochloric acid is removed by first washing with a base, such as sodium hydroxide, followed by washing with water.

The reaction time, in its turn, is selected as a function of the working temperature: thus one passes from 10 to 30 hours at a temperature of 25° C. to 30 to 60 minutes at a temperature of 37° C. There is, in practice, an inverse relationship between the temperature within the range considered above and the reaction time; these two parameters must be accurately coordinated in order that the desired values may be obtained, inasmuch as lower values of the temperature require longer reaction times.

As regards the starting materials, it is possible to start from any kind of material of a polyamide nature: polycaprolactam and the various types of aliphatic or aromatic nylons are especially advisable. The treatment consists, in practice, in introducing on the surface of such materials, an infinity of dipoles the overall charge of which is zero.

Inasmuch as the procedure which renders the articles made with these materials biocompatible is a bland superficial hydrolysis, it can be surmised that any chemical modification undergone by biocompatible articles of this kind (provided that it is a nondestructive modification, of course) will not impair the characteristics of biocompatibility of the material concerned.

It is possible to select, from among the wide host of existing polyamides, materials which lend themselves to different uses. It becomes thus possible to exploit articles which range from those adapted from long-lasting protheses to thin membranes which are gas-pervious and can be used for heart-lung machines and for artificial kidneys.

The articles can be made starting from an already modified polyamide, or the modification can be carried out on an already shaped article. In addition, the polyamide can be admixed with one or more conventional ingredients.

The invention is described in detail with the aid of the following examples which are not to be construed as limitations.

EXAMPLE 1

5 Meters of Nylon-6 thread (dia. 0.25 mm, commercial polycaprolactam) have been twice extracted with dioxan and petroleum ether (40/60 by vol), under reflux conditions for two hours. The thread has been subsequently washed, first with acetone and then with water, whereafter it has been subjected to a superficial hydrolysis with HCl (3 time normal=3 N) at 37° C. The hydrolysis last 30 minutes, whereafter the thread has been washed with 0.1 N NaOH and then with water.

The completion of the hydrolysis and thus the presence of amine groups on the surface of the thread has been confirmed by colorimetric assays. A sample of the thread has been immersed in a 0.1% (wt/vol) solution of trinitrobenzenesulfonic acid in saturated tetraborate and, after one hour, it took a yellow-reddish hue, whereas a reference sample which had not been hydrolized did not take any color. The hydrolized nylon thread thus obtained has been carefully and evenly wrapped around an intravenous Teflon (R.T.M.) catheter (Wallace, length 30 cm, I.D.. 0.69 mm, O.D. 1.14 mm) so as to cover the surface satisfactorily. A similar comparison catheter has been prepared by using a non-hydrolized nylon thread. The two catheters have been inserted in the femoral veins of a medium-size dog kept under general aneasthesia (Pentothan, R.T.M.), free breathing. A collateral of the femoral vein has been isolated, and a probe has been introduced along the entire length of the collateral so that a predominant portion of the probe was floating in the iliac vein and in the inferior vena cava. The end of the probe has been tied to the collateral branch of the femoral vein and covered by the muscle bundles. Eventually, the wound has been stitched. In the same way, the second probe has been introduced in the other femoral vein of the test animal. Both before and after the operation, heparin has been administered to the animal to prevent vascular thrombi due to the surgical wounds. The probes have been left in situ for 30 days without administering any further anticoagulants: on completion of this period, the animal has been killed and the probes withdrawn. The probe having the hydrolized nylon thread wrapper has been found clean and clot-free. Also the vascular wall was found in good conditions. The reference probe with the untreated nylon thread wrapper, conversely, has been found coated by numerous thrombi.

EXAMPLE 2

3 Meters of tube of Nylon-66 (O.D. 9 mm, I.D. 7 mm) have been subjected to superficial hydrolysis by having a 3% solution of HCl flowing therethrough at 37° C. for about one hour. On completion of the reaction, the tube has been washed with decinormal (0.1 N) NaOH and then with water. The completion of the hydrolysis has been confirmed by the colorimetric procedure described in the previous Example. The test of platelet adhesiveness has been carried out on sections of hydrolized nylon tube and on sections of untreated nylon tubes. The method of A. J. Hellem ("Platelet adhesiveness in von Willebrand's disease". A study with a new modification of the glass bead filter method, Scand. J. Haemat, 7, 374, 1970) has been followed by using native blood of a healthy individual, drawn and caused to flow through the tubes being tested by means of a pump having a rate of delivery of 4 mls per minute. Platelet counts have been made both before and after the flow of the blood through the nylon tubes.

The counts have been made by collecting blood samples in an aqueous solution containing bipotassic EDTA at the concentration of 6 milligrams per 10 milliliters.

The platelet count has been made with a phase contrast microscope according to the method of Brecher and Cronkite (Morphology and enumeration of human blood platelets, J. Appl. Physiol. 3, 365, 1950).

In the case of hydrolized Nylon tubes, no significant decrease has been observed of the number of platelets in solution. On the contrary, on the untreated Nylon tubes, the platelet adhesiveness was 56.5%.

EXAMPLE 3

Rings of Nylon-66 have been prepared (length 9 mm, I.D. 7 mm, O.D. 8 mm) and special care has been taken in machining the edges, which have been beveled and rounded. A certain number of such rings has been hydrolized with HCl (3.5 normal) at 37° C., for one hour. Also in this case, the completeness of the hydrolysis has been confirmed by the trinitrobenzene sulfonate tests. The rings of superficially hydrolyzed Nylon and other comparison rings have been inserted in the inferior vena cava of dogs of medium size by a thoracotomy under general anaesthesia (Nembutal, R.T.M.). Special care has been taken when inserting the rings. Care has been taken that the rings did not contact the atrium wall and that the vein wall was not damaged too much when inserting the ring. It has been observed that the reference rings, after two hours, already exhibited numerous clots stuck to the walls and in some cases, even the obstruction of the prothesis has been experienced. The hydrolized nylon rings, conversely, have been withdrawn after two weeks, cleaned and only in few cases a few thrombi have been seen on the inner ring wall.

We claim:

1. A process for the preparation of a biocompatible polyamide material, said process consisting essentially of subjecting a polyamide material to superficial hydrolysis by reacting said polyamide material with a 3 to 4 normal hydrogen chloride solution and removing substantially all unreacted hydrogen chloride by first washing with a base and then washing with water.

2. The process of claim 1 wherein said base is sodium hydroxide.

3. The process of claim 1 characterized in that the reaction is conducted at a temperature of from 20° C. to 40° C.

4. The process of claim 3 wherein the reaction is conducted at a temperature of 25° C. for a time ranging from 10 to 30 hours.

5. The process of claim 3 wherein the reaction is conducted at a temperature of 37° C. for a time ranging from 30 to 60 minutes.

6. The process of claim 1 wherein said polyamide material is selected from the group consisting of aliphatic nylon and aromatic nylon.

7. The process of claim 6 wherein said aliphatic nylon is polycaprolactam.

8. A shaped biocompatible article of manufacture from a polyamide that has been prepared according to the process of claim 1.

9. The shaped biocompatible article of claim 8 in the form of a prothesis or a membrane.

* * * * *